United States Patent
Yu et al.

(10) Patent No.: US 10,966,831 B2
(45) Date of Patent: Apr. 6, 2021

(54) DELIVERY DEVICE FOR PROSTHETIC MITRAL VALVE ANNULOPLASTY RING AND PROSTHETIC MITRAL VALVE ANNULOPLASTY RING DELIVERY SYSTEM

(71) Applicant: SHANGHAI NEWMED MEDICAL CO., LTD., Shanghai (CN)

(72) Inventors: Qifeng Yu, Shanghai (CN); Lihong Hou, Shanghai (CN); Zhijie Wang, Shanghai (CN); Haishan Wang, Shanghai (CN); Tao Qin, Shanghai (CN)

(73) Assignee: Shanghai Newmed Medical Co., Ltd., Shanghai (CN)

( * ) Notice: Subject to any disclaimer, the term of this patent is extended or adjusted under 35 U.S.C. 154(b) by 254 days.

(21) Appl. No.: 16/336,866

(22) PCT Filed: Nov. 25, 2016

(86) PCT No.: PCT/CN2016/107280
§ 371 (c)(1),
(2) Date: Mar. 26, 2019

(87) PCT Pub. No.: WO2018/053928
PCT Pub. Date: Mar. 29, 2018

(65) Prior Publication Data
US 2019/0247192 A1 Aug. 15, 2019

(30) Foreign Application Priority Data
Sep. 26, 2016 (CN) .......................... 201610852365.6

(51) Int. Cl.
*A61F 2/24* (2006.01)
*A61F 2/95* (2013.01)

(52) U.S. Cl.
CPC .......... *A61F 2/2466* (2013.01); *A61F 2/2448* (2013.01); *A61F 2002/9505* (2013.01)

(58) Field of Classification Search
CPC .... A61F 2/2442; A61F 2/2445; A61F 2/2448; A61F 2/2466; A61F 2002/9505
See application file for complete search history.

(56) References Cited

U.S. PATENT DOCUMENTS

| 8,500,792 | B2 * | 8/2013 | Berra | A61F 2/07 623/1.12 |
| 2005/0080476 | A1 * | 4/2005 | Gunderson | A61F 2/966 623/1.11 |

(Continued)

FOREIGN PATENT DOCUMENTS

| CN | 202908881 U | 5/2013 |
| CN | 203506933 U | 4/2014 |

(Continued)

*Primary Examiner* — Ashley L Fishback
(74) *Attorney, Agent, or Firm* — Muncy, Geissler, Olds & Lowe, P.C.

(57) ABSTRACT

A prosthetic mitral annuloplasty ring includes a wire, an adjustment member for changing a length of the wire and a jacketing annulus for adjusting a radial dimension of the mitral valve annuloplasty ring. The jacketing annulus is sleeved over the wire and forms, together with the adjustment member, a shape matching that of a native mitral valve annulus. After the prosthetic mitral annuloplasty ring is implanted by suturing in a conventional surgical procedure and the patient's heart starts to beat again, the adjustment member can be connected to the delivery device and the wire length therein can be adjusted by a rotating operation of the delivery device so that the mitral valve annuloplasty ring will be expanded or contracted until the prosthetic mitral annuloplasty ring perfectly fits the native mitral valve annulus in shape, effectively avoiding the problem of incomplete mitral leaflet coaptation.

20 Claims, 4 Drawing Sheets

(56) References Cited

U.S. PATENT DOCUMENTS

| | | |
|---|---|---|
| 2005/0107871 A1 | 5/2005 | Realyvasquez et al. |
| 2007/0027533 A1 | 2/2007 | Douk |
| 2007/0244555 A1 | 10/2007 | Rafiee et al. |
| 2012/0022644 A1* | 1/2012 | Reich .................. A61B 17/068 623/2.37 |
| 2013/0116776 A1 | 5/2013 | Gross et al. |
| 2013/0116780 A1 | 5/2013 | Miller et al. |

FOREIGN PATENT DOCUMENTS

| | | |
|---|---|---|
| CN | 105105870 A | 12/2015 |
| CN | 105326582 A | 2/2016 |
| CN | 105769388 A | 7/2016 |
| WO | WO 02022026 A1 | 3/2002 |
| WO | WO 2007/035882 A2 | 3/2007 |
| WO | WO 2012/019052 A2 | 2/2012 |

* cited by examiner

DELIVERY DEVICE FOR PROSTHETIC MITRAL VALVE ANNULOPLASTY RING AND PROSTHETIC MITRAL VALVE ANNULOPLASTY RING DELIVERY SYSTEM

TECHNICAL FIELD

The present invention relates to medical devices and, in particular, to a delivery device for delivering a prosthetic mitral annuloplasty ring and a prosthetic mitral annuloplasty ring delivery system.

BACKGROUND

Mitral valve annuloplasty treats heart valve diseases featuring mitral valve regurgitation by implanting a prosthetic mitral annuloplasty ring. As part of the surgical technique, the prosthetic ring can help repair heart valve defects (e.g., incomplete mitral leaflet coaptation). The mitral valve consists of the mitral valve annulus, leaflets, papillary muscles and chordae tendineae. Mitral regurgitation is the abnormal leaking of blood backwards from the left ventricle into the left atrium, when the left ventricle contracts. Stretching of the mitral valve annulus may compromise the competence of the valve, leading to a distortion of the normal shape of the valve orifice.

As key part mitral valve annuloplasty, the prosthetic mitral annuloplasty ring must have a suitable size and shape to allow the mitral valve annulus to regain the normal shape which is considered a prerequisite for good leaflet coaptation. However, in the current practice, the choice of the prosthetic mitral annuloplasty ring largely depends on the physician' personal experience and preferences. A small size of the prosthetic mitral annuloplasty ring may cause mitral valve stenosis, while too large size of the prosthetic mitral annuloplasty ring can lead to undesirable leaflet coaptation height and areas which may adversely affect annuloplasty outcomes.

Since traditional mitral valve annuloplasty procedures require cardiopulmonary bypass with the heart arrested, it is difficult to accurately measure the size of the mitral annulus and assess the repair outcome. In view of this, the present invention improves conventional mitral valve annuloplasty rings and avoids their drawbacks by additionally including an adjustable member on the prosthetic mitral annuloplasty ring. Wherein the adjustable member is connected to a specific delivery device for the prosthetic mitral annuloplasty ring. Using the delivery device for the prosthetic mitral annuloplasty ring allows the physician to effect in time a secondary adjustment in the ring size and shape during the implantation procedure as needed for a good surgical outcome.

SUMMARY OF THE INVENTION

It is an objective of the present invention to overcome the prior art problem of absence of delivery means capable of resizing mitral valve annuloplasty rings by presenting a device and system for delivering a prosthetic mitral annuloplasty ring.

To this end, the device provided in the present invention is for delivering a prosthetic mitral annuloplasty ring, the prosthetic mitral annuloplasty ring includes an adjustment member which is configured to adjust a size of the prosthetic mitral annuloplasty ring and provided with an internal thread, the delivery device for the prosthetic mitral annuloplasty ring comprising a driving member and a connecting member disposed at a distal end of the driving member.

The connecting member includes an outer tube, an intermediate tube and an adjusting core. The driving member includes an intermediate tube knob for adjusting a position of the intermediate tube and a core knob for adjusting a position of the adjusting core.

The outer tube has one end fixed to the distal end of the driving member and the other end configured to be fixed to the adjustment member.

The intermediate tube has a first end connected to the intermediate tube knob and a second end passing through a body of the outer tube along an axial direction of the outer tube, such that a portion of the intermediate tube is exposed, wherein the portion of the intermediate tube exposed from the outer tube is provided with an external thread complementary to the internal thread of the adjustment member, and the intermediate tube is movable within the body of the outer tube through manipulation of the intermediate tube knob.

The adjusting core has a first end connected to the core knob and a second end passing through a body of the intermediate tube along an axial direction of the intermediate tube, the adjusting core being able to telescope within the body of the intermediate tube through manipulation of the core knob.

Optionally, the device may further include a fixing claw for fixing the prosthetic mitral annuloplasty ring to the outer tube at a distal end of the outer tube.

Optionally, in the device, the fixing claw may be fabricated from a nickel titanium alloy, a medical grade stainless steel or a cobalt-based alloy.

Optionally, the device may further include a sliding block for driving the intermediate tube to move, the intermediate tube knob being connected to the first end of the intermediate tube through the sliding block, wherein the intermediate tube is movable within the body of the outer tube through manipulation of the intermediate tube knob to engage the external thread on the intermediate tube with the internal thread of the adjustment member.

Optionally, in the device, driving member may further include a graduated indicator showing a status of the core knob.

Optionally, in the device, the adjusting core may include a first core segment and a second core segment, the first core segment connected to the driving member at one end and coupling with the second core segment at the other end.

Optionally, in the device, the first core segment may be a circular cylinder, with the second core segment having a rectangular, cross-shape or star-shaped cross-section.

Optionally, in the device, the intermediate tube may include a first section and a second section coupling with the first section, the first section of the intermediate tube passing through the body of the outer tube along the axial direction of the outer tube, the second section of the intermediate tube projecting out of the body of the outer tube, and wherein the external thread is formed on a wall of the second section of the intermediate tube.

Optionally, in the device, the adjusting core may be fabricated from a nickel titanium alloy, a medical grade stainless steel or a cobalt-based alloy.

The present invention also provides a system for delivering a prosthetic mitral annuloplasty ring, including the device as defined above and the prosthetic mitral annuloplasty ring that is connected at a distal end of the device, the prosthetic mitral annuloplasty ring includes an adjustment member which is configured to resize the prosthetic mitral annuloplasty ring and provided with an internal thread.

Optionally, in the system, the prosthetic mitral annuloplasty ring may further include a wire and a jacketing annulus which is sleeved over the wire and forms, together with the adjustment member, a shape matching a shape of a native mitral valve annulus.

Optionally, in the system, the adjustment member may include a housing, a spool accommodated within the housing and adapted to wind a portion of the wire thereon, a washer for securing the spool and a damper for restraining a wound wire portion, the washer and the damper disposed on opposing sides of the spool, the spool provided with a revolving shaft disposed along an axial direction thereof, the washer defining an opening through which the revolving shaft projects and is anchored to the adjusting core.

In the device and system provided in the present invention, based on the specific structures of the driving member and of the connecting member disposed at the distal end of the driving member, in practical use, the outer tube is fixed to the prosthetic mitral annuloplasty ring, and the external thread on the intermediate tube is engaged with the internal thread in the adjustment member by a rotating operation. The adjusting core is then driven to be anchored at one end to the adjustment member so that a rotating operation can result in a change in the adjustment member and thus in the size of the prosthetic mitral annuloplasty ring. Therefore, the device of the present invention can not only deliver the prosthetic mitral annuloplasty ring but can also allow resizing the prosthetic mitral annuloplasty ring that has been delivered to a target site according to the practical need to achieve a better mitral valve annuloplasty outcome.

In these figures: 1—prosthetic mitral annuloplasty ring; 10—adjustment member; 11—spool; 12—washer; 13—revolving shaft; 14—internal thread; 2—delivery device for the prosthetic mitral annuloplasty ring; 20—driving member; 200—core knob; 201—intermediate tube knob; 202—graduated indicator; 21—connecting member; 210—outer tube; 211—intermediate tube; 212—adjusting core; 213—fixing claw; 214—external thread.

DETAILED DESCRIPTION OF PREFERRED EMBODIMENTS

The prosthetic mitral annuloplasty ring delivery device and system proposed in the present invention will be described in greater detail below with reference to specific embodiments which are to be read in conjunction with the accompanying drawings. Features and advantages of the invention will be more readily apparent from the following detailed description, and from the appended claims. Note that the figures are provided in a very simplified form not necessarily presented to scale, with the only intention of facilitating convenience and clarity in explaining the embodiments.

Figure 1:
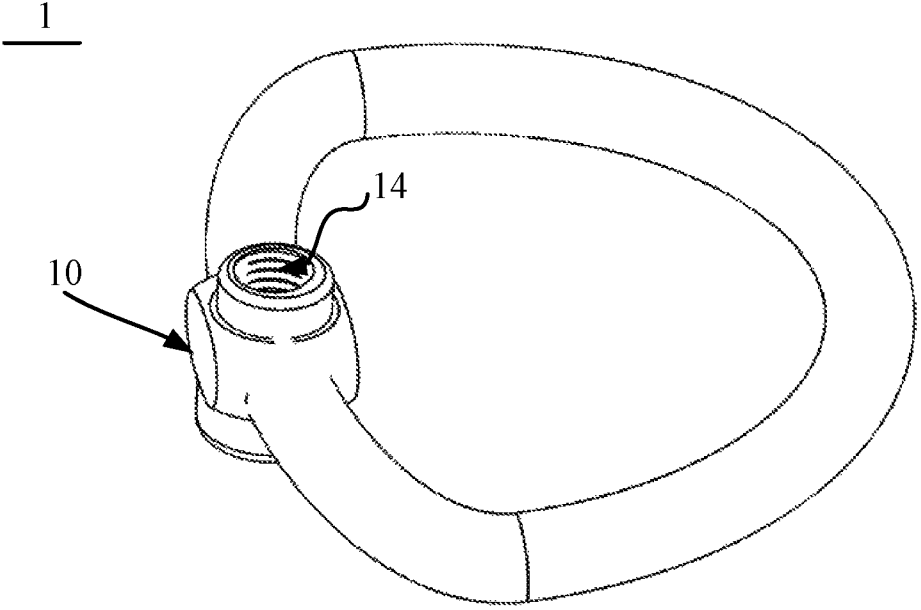
FIG. 1 schematically illustrates a prosthetic mitral annuloplasty ring according to an embodiment of the present invention.
Figure 2:
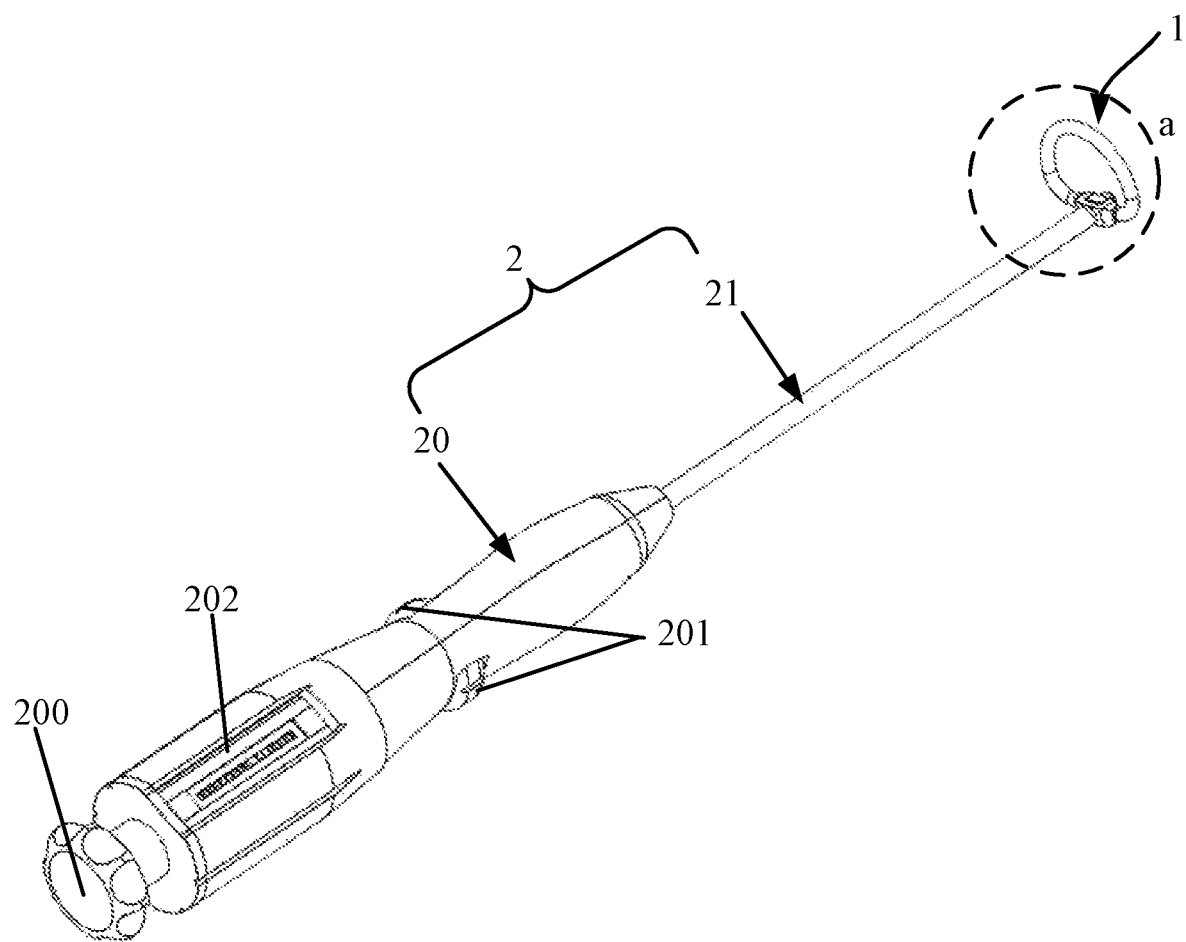
FIG. 2 is a schematic illustration of a system for delivering the prosthetic mitral annuloplasty ring according to an embodiment of the present invention.

Disclosed herein is a device and system for a prosthetic mitral annuloplasty ring capable of repairing a defective mitral valve so that it regains its normal physiological shape and configuration. Reference is now made to FIGS. 1 and 2. FIG. 1 schematically shows a prosthetic mitral annuloplasty ring according to an embodiment of the invention, and FIG. 2 is a schematic illustration of a system for delivering the prosthetic mitral annuloplasty ring according to an embodiment of the invention. As shown in FIG. 2, the prosthetic mitral annuloplasty ring delivery system includes a delivery device 2 for the prosthetic mitral annuloplasty ring and the prosthetic mitral annuloplasty ring 1 that is connected to a distal end of the delivery device 2 for the prosthetic mitral annuloplasty ring. The prosthetic mitral annuloplasty ring 1 includes an adjustment member 10 (see FIG. 1) with an internal thread 14, which is adapted to resize the annuloplasty ring. As used herein, the term "distal end" refers to an end facing away from the operator and the term "proximal end" means an end close to the operator.

The prosthetic mitral annuloplasty ring 1 also includes a wire and a jacketing annulus that is sleeved over the wire and forms, together with the adjustment member 10, a shape matching that of a native mitral valve annulus. After the prosthetic mitral annuloplasty ring has been implanted by a conventional suturing procedure, a length of the wire sleeved in the jacketing annulus can be changed by manipulating the adjustment member 10 to cause the jacketing annulus to radially contract or expand. In this way, the prosthetic mitral annuloplasty ring 1 can be adjusted in size and shape to accurately fit the native mitral valve annulus.

Figure 3:
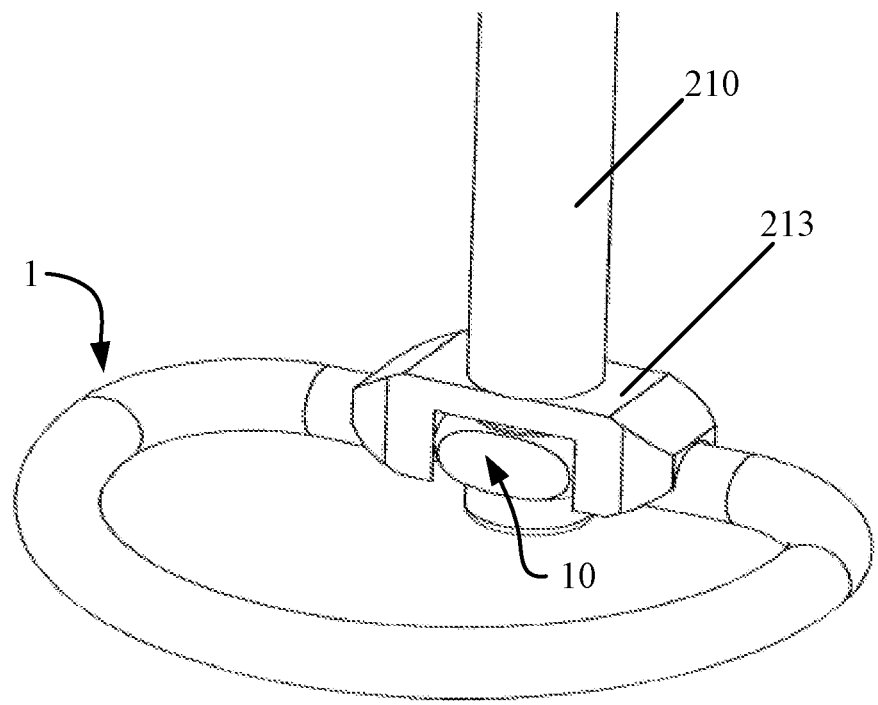
FIG. 3 is an enlarged schematic view of portion a of FIG. 2.
Figure 4:
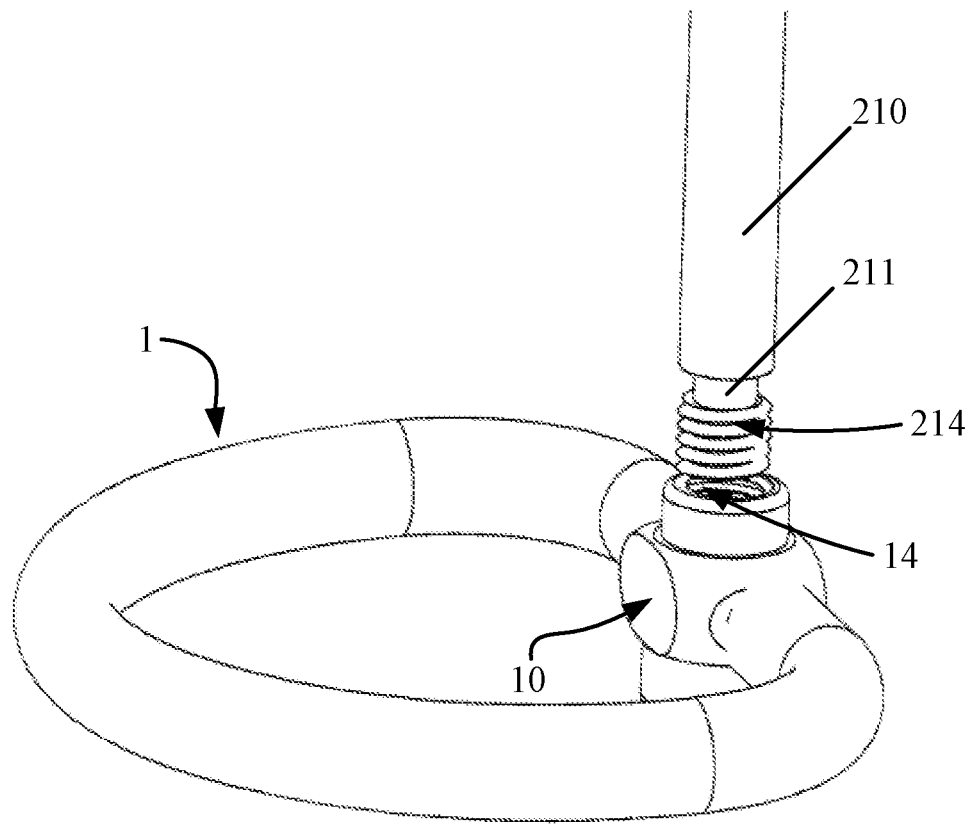
FIG. 4 is an enlarged schematic view showing the engagement between an external thread on an intermediate tube and an internal thread of an adjustment member of FIG. 3.
Figure 5:
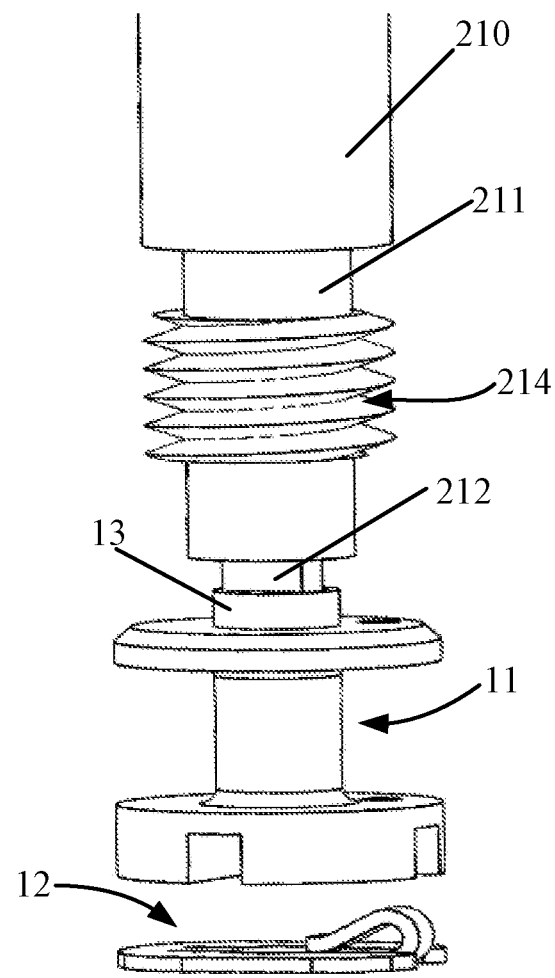
FIG. 5 schematically shows an adjusting core anchored to the adjustment member of FIG. 3.

Reference is now made to FIGS. 3, 4 and 5. FIG. 3 is an enlarged schematic view of portion a of FIG. 2. FIG. 4 is an enlarged schematic view showing the engagement between an external thread on an intermediate tube and the internal thread of the adjustment member of FIG. 3. FIG. 5 schematically shows an adjusting core anchored to the adjustment member of FIG. 3. The adjustment member 10 includes a housing, a spool 11 accommodated within the housing and adapted to wind a portion of the wire thereon, a washer 12 for securing the spool 11 and a damper for restraining the wound wire portion. The washer 12 and the damper are disposed on opposing sides of the spool 11. In order to wind the wire portion onto the spool 11 as the spool 11 rotates, the spool 11 is provided with a revolving shaft 13 disposed along the center axis thereof. The washer 12 defines an opening through which the revolving shaft 13 can project and be anchored to the adjusting core as an initial step of subsequent docking of the adjustment member 10 to the delivery device 2 for the prosthetic mitral annuloplasty ring. The internal thread 14 of the adjustment member 10 is formed within the housing.

Figure 6:
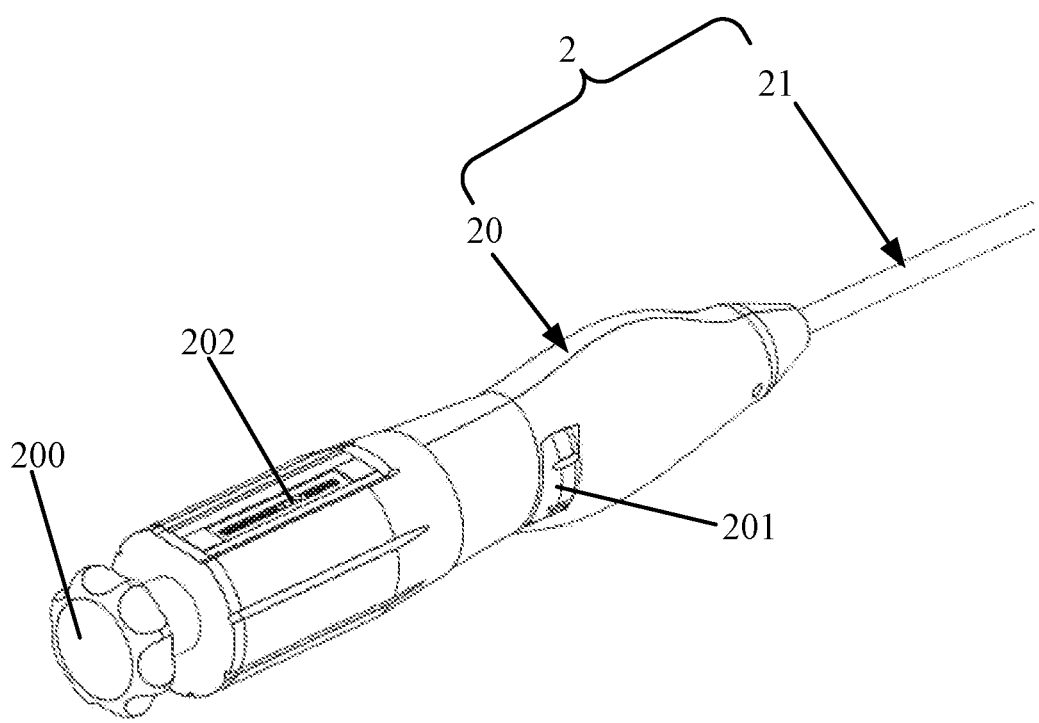
FIG. 6 schematically shows a driving member in a device for delivering the prosthetic mitral annuloplasty ring according to an embodiment of the present invention.

Referring to FIGS. 4 and 6, the delivery device 2 for the prosthetic mitral annuloplasty ring includes a driving member 20 and a connecting member 21 coupled to a distal end of the driving member 20. The connecting member 21 includes an outer tube 210, the intermediate tube 211 and the adjusting core 212. The driving member 20 includes an intermediate tube knob 201 for moving the intermediate tube 211 and a core knob 200 for moving the adjusting core 212. One end of the outer tube 210 is fixed to the distal end of the driving member 20 and the other end of the outer tube 210 is fixed to the adjustment member 10. One end of the intermediate tube 211 is connected to the intermediate tube knob 201 and the other end of the intermediate tube 211 projects out of the outer tube 210 along the axial direction of the outer tube 210, such that a portion of the intermediate tube 211 is exposed. On the portion of the intermediate tube 211 exposed from the outer tube 210 is provided with the external thread 214 complementary to the internal thread 14 of the adjustment member 10. The intermediate tube 211 is movable within the outer tube 210 when the intermediate tube knob 201 is turned. The adjusting core 212 is connected at one end to the core knob 200 and the other end of the adjusting core 212 penetrates through the intermediate tube 211 along the axial direction of the intermediate tube 211. When the core knob 200 is manipulated, the adjusting core 212 will telescope within the intermediate tube 211. In this embodiment, the driving member is preferably a handle, and the outer tube may be made of HDPE or PP.

As shown in FIG. 6, the driving member 20 may further include a graduated indicator 202 showing the status of the core knob 200. In this embodiment, the core knob 200 may be turned clockwise or counterclockwise. When the core knob 200 is turned clockwise or counterclockwise, the adjusting core 212 will rotate accordingly with the core knob 200 in the same direction. The graduated indicator 202 provides operator with an instantaneous and intuitive indication of an inner diameter of the prosthetic mitral annuloplasty ring. Specifically, a scale in the graduated indicator 202 indicates a distance that the indicator has translated. The distance is positively correlated to the number of turns that the knob has been rotated, which is in turn positively correlated to the length of the wire that has been wounded onto the spool. From this length, a change in the size of the prosthetic mitral annuloplasty ring, i.e., its amount of expansion or contraction, can be inferred.

More specifically, when the core knob 200 is manipulated, the adjusting core will rotate, exerting a force on the revolving shaft anchored thereto, which drives the spool to rotate in the same direction as the adjusting core. As a result, the wire is wound onto or unwound from the spool, causing the jacketing annulus sleeved over the wire to be expanded or contracted, i.e., leading to a change in the overall size of the prosthetic mitral annuloplasty ring. In this embodiment, the overall size of the prosthetic mitral annuloplasty ring changes because the configuration of the jacketing annulus varies with the length of the wire sleeved therein—the jacketing annulus is expanded when the wire portion becomes longer and contracted when the wire portion is shortened. Thus, when the core knob 200 drives the adjusting core to rotate counterclockwise, the spool also rotates counterclockwise so that the aforementioned wire length becomes longer and expands the jacketing annulus; and vice versa. The relationship between the direction of rotation of the spool and the configuration of the jacketing annulus includes, but is not limited to the aforementioned. Rather, it depends on the how the wire is wounded onto the spool.

With continued reference to FIG. 3, the delivery device for the prosthetic mitral annuloplasty ring may further include a fixing claw 213 for fixing the prosthetic mitral annuloplasty ring 1 to the outer tube 210. The fixing claw 213 is arranged at a distal end of the outer tube 210. As a medium for the fixed connection between the outer tube 210 and prosthetic mitral annuloplasty ring 1, the fixing claw 213 keeps the outer tube 210 stationary relative to the prosthetic mitral annuloplasty ring 1, enabling the alignment and engagement between the thread on the intermediate tube 211 and the internal thread 14 of the adjustment member 10.

Preferably, the fixing claw may be fabricated from a nickel titanium alloy, a medical grade stainless steel or a cobalt-based alloy.

The delivery device for the prosthetic mitral annuloplasty ring may further include a sliding block (not shown) for driving the intermediate tube 211 to move. The intermediate tube knob is connected to the aforementioned end of the intermediate tube 211 through this sliding block. By manipulating the intermediate tube knob 201, the intermediate tube 211 can be moved within the outer tube 210 through manipulation of the intermediate tube knob to engage the external thread 214 on the intermediate tube 211 with the internal thread 14 of the adjustment member.

In this embodiment, the adjusting core 212 may include a first core segment and a second core segment. The first core segment is connected to the driving member 20 at one end and couples with the second core segment at the other end. Preferably, the first core segment is a circular cylinder received within the intermediate tube in order to define a movement range for the adjusting core. The second core segment may have, but is not limited to, a rectangular, cross-shape or star-shaped cross-section. A suitable cross-sectional shape may be selected according to the structure of the revolving shaft in the adjustment member so as to allow the second core segment to be aligned with and anchored to the revolving shaft of the adjustment member during the docking of the adjustment member to the delivery device for the prosthetic mitral annuloplasty ring. Preferably, the adjusting core may be fabricated from a nickel-titanium alloy, a medical grade stainless steel or a cobalt-based alloy.

Further, the intermediate tube may include a first section and a second section coupling with the first section. The first section of the intermediate tube axially extends through the outer tube, while the second section thereof projects out of the outer tube. The external thread is formed on the wall of the second section. When the external thread on the second section of the intermediate tube engages with the internal thread formed in an internal surface of the housing of the adjustment member, a channel is created for accommodating movement required for the docking between the adjusting core and the adjustment member. Preferably, the intermediate tube may be made of HDPE or PP.

With continued reference to FIG. 5, the docking between the delivery device for the prosthetic mitral annuloplasty ring and the adjustment member is accomplished by the mating between the delivery device for the prosthetic mitral annuloplasty ring and the revolving shaft 13 in the adjustment member, which allows adjusting the adjustment member through the delivery device for the prosthetic mitral annuloplasty ring. Preferably, the revolving shaft 13 is a recessed structure, and more preferably, a recessed structure resembling a slot screw head. The end of the delivery device for the prosthetic mitral annuloplasty ring that mates with the revolving shaft 13 defines a protrusion complementary to the recessed structure in shape. In case of the recessed structure resembling a slot screw head, the protrusion will resemble the work end of a suitable slot screwdriver. In this embodiment, the protrusion is provided at a distal end of the adjusting core. The connecting member may be a flexible structure, and the delivery device for the prosthetic mitral annuloplasty ring may have an extension sheath made of a flexible or rigid material. Here, a flexible material is preferred in order to facilitate adjusting the size and shape of the prosthetic mitral annuloplasty ring and enable delivery thereof in a crimped configuration if actually needed.

With combined reference to FIGS. 1, 2 and 5, it will be appreciated the delivery device for the prosthetic mitral annuloplasty ring of the present invention can be used in the following manner.

First of all, the outer tube 210 is fixed to the prosthetic mitral annuloplasty ring 1 through the fixing claw 213 at the distal end of the outer tube 210.

The intermediate tube knob 201 is then manipulated to cause the intermediate tube 211 axially move into alignment between the external thread 214 on the intermediate tube 211 and the internal thread 14 of the adjustment member 10, followed by engagement of the two threads.

After the prosthetic mitral annuloplasty ring 1 has been delivered to a target site under the action of the driving member 20, if it is necessary to adjust the size of the prosthetic mitral annuloplasty ring 1, the core knob 200 is manipulated to cause the adjusting core 212 to move so that its aforementioned end is anchored to the revolving shaft 13 in the adjustment member 10. The core knob 200 is then rotated in a predetermined direction, causing the adjusting core 212 and hence the spool 11 over the revolving shaft 13 to which the adjusting core 212 is anchored to rotate in the same direction. This brings about a change in the wire length and thus in the annuloplasty ring size.

In summary, in the device and system of the present invention for delivering a prosthetic mitral annuloplasty ring capable of repairing a defective mitral valve so that it regains its normal physiological shape and configuration, based on the specific structures of the driving member and of the connecting member disposed at the distal end of the driving member, in practical use, the outer tube is fixed to the prosthetic mitral annuloplasty ring, and the external thread on the intermediate tube is engaged with the internal thread in the adjustment member by a rotating operation. The adjusting core is then driven to be anchored at one end to the adjustment member so that a rotating operation can result in a change in the adjustment member and thus in the size of the prosthetic mitral annuloplasty ring. Therefore, the device of the present invention can not only deliver the prosthetic mitral annuloplasty ring but can also allow resizing the prosthetic mitral annuloplasty ring that has been delivered to a target site according to the practical need to achieve a better mitral valve annuloplasty outcome.

The description presented above is merely that of a few preferred embodiments of the present invention and does not limit the scope thereof in any sense. Any and all changes and modifications made by those of ordinary skill in the art based on the above teachings fall within the scope as defined in the appended claims.

What is claimed is:

1. A delivery device for a prosthetic mitral annuloplasty ring, the prosthetic mitral annuloplasty ring comprising an adjustment member which is configured to adjust a size of the prosthetic mitral annuloplasty ring and provided with an internal thread, the delivery device for the prosthetic mitral annuloplasty ring comprising a driving member and a connecting member disposed at a distal end of the driving member, wherein:

the connecting member comprises an outer tube, an intermediate tube and an adjusting core, the driving member comprising an intermediate tube knob for adjusting a position of the intermediate tube and a core knob for adjusting a position of the adjusting core;

the outer tube has one end fixed to the distal end of the driving member and the other end configured to be fixed to the adjustment member;

the intermediate tube has a first end connected to the intermediate tube knob and a second end passing through a body of the outer tube along an axial direction of the outer tube, such that a portion of the intermediate tube is exposed, wherein the portion of the intermediate tube exposed from the outer tube is provided with an external thread complementary to the internal thread of the adjustment member, and the intermediate tube is movable within the body of the outer tube through manipulation of the intermediate tube knob; and the adjusting core has a first end connected to the core knob and a second end passing through a body of the intermediate tube along an axial direction of the intermediate tube, the adjusting core being able to telescope within the body of the intermediate tube through manipulation of the core knob.

2. The delivery device for a prosthetic mitral annuloplasty ring of claim 1, further comprising a fixing claw for fixing the prosthetic mitral annuloplasty ring to the outer tube at a distal end of the outer tube.

3. The delivery device for a prosthetic mitral annuloplasty ring of claim 2, wherein the fixing claw is fabricated from a nickel titanium alloy, a medical grade stainless steel or a cobalt-based alloy.

4. The delivery device for a prosthetic mitral annuloplasty ring of claim 1, further comprising a sliding block for driving the intermediate tube to move, the intermediate tube knob being connected to the first end of the intermediate tube through the sliding block, wherein the intermediate tube is movable within the body of the outer tube through manipulation of the intermediate tube knob to engage the external thread on the intermediate tube with the internal thread of the adjustment member.

5. The delivery device for a prosthetic mitral annuloplasty ring of claim 1, wherein the driving member further comprises a graduated indicator showing a status of the core knob.

6. The delivery device for a prosthetic mitral annuloplasty ring of claim 1, wherein the adjusting core comprises a first core segment and a second core segment, the first core segment connected to the driving member at one end and coupling with the second core segment at the other end.

7. The delivery device for a prosthetic mitral annuloplasty ring of claim 6, wherein the first core segment is a circular cylinder, and the second core segment has a rectangular, cross-shape or star-shaped cross-section.

8. The delivery device for a prosthetic mitral annuloplasty ring of claim 1, wherein the intermediate tube comprises a first section and a second section coupling with the first section, the first section of the intermediate tube passing through the body of the outer tube along the axial direction of the outer tube, the second section of the intermediate tube projecting out of the body of the outer tube, and wherein the external thread is formed on a wall of the second section of the intermediate tube.

9. The delivery device for a prosthetic mitral annuloplasty ring of claim 1, wherein the adjusting core is fabricated from a nickel titanium alloy, a medical grade stainless steel or a cobalt-based alloy.

10. A delivery system for a prosthetic mitral annuloplasty ring, comprising a delivery device for a prosthetic mitral annuloplasty ring and a prosthetic mitral annuloplasty ring that is connected at a distal end of the delivery device for the prosthetic mitral annuloplasty ring, the prosthetic mitral annuloplasty ring comprising an adjustment member which is configured to adjust a size of the prosthetic mitral annuloplasty ring and provided with an internal thread, the delivery device for the prosthetic mitral annuloplasty ring comprising a driving member and a connecting member disposed at a distal end of the driving member, wherein:

the connecting member comprises an outer tube, an intermediate tube and an adjusting core, the driving member comprising an intermediate tube knob for adjusting a position of the intermediate tube and a core knob for adjusting a position of the adjusting core;

the outer tube has one end fixed to the distal end of the driving member and the other end configured to be fixed to the adjustment member;

the intermediate tube has a first end connected to the intermediate tube knob and a second end passing through a body of the outer tube along an axial direction of the outer tube, such that a portion of the intermediate tube is exposed, wherein the portion of the intermediate tube exposed from the outer tube is provided with an external thread complementary to the internal thread of the adjustment member, and the intermediate tube is movable within the body of the outer tube through manipulation of the intermediate tube knob; and the adjusting core has a first end connected to the core knob and a second end passing through a body of the intermediate tube along an axial direction of the intermediate tube, the adjusting core being able to telescope within the body of the intermediate tube through manipulation of the core knob.

11. The delivery system for a prosthetic mitral annuloplasty ring of claim 10, wherein the prosthetic mitral annuloplasty ring further comprises a wire and a jacketing annulus which is sleeved over the wire and forms, together with the adjustment member, a shape matching a shape of a native mitral valve annulus.

12. The delivery system for a prosthetic mitral annuloplasty ring of claim 11, wherein the adjustment member comprises a housing, a spool accommodated within the housing and adapted to wind a portion of the wire thereon, a washer for securing the spool and a damper for restraining a wound wire portion, the washer and the damper disposed on opposing sides of the spool, the spool provided with a revolving shaft disposed along an axial direction thereof, the washer defining an opening through which the revolving shaft projects and is anchored to the adjusting core.

13. The delivery system for a prosthetic mitral annuloplasty ring of claim 10, wherein the delivery device for the prosthetic mitral annuloplasty ring further comprises a fixing claw for fixing the prosthetic mitral annuloplasty ring to the outer tube at a distal end of the outer tube.

14. The delivery system for a prosthetic mitral annuloplasty ring of claim 13, wherein the fixing claw is fabricated from a nickel titanium alloy, a medical grade stainless steel or a cobalt-based alloy.

15. The delivery system for a prosthetic mitral annuloplasty ring of claim 10, wherein the delivery device for the prosthetic mitral annuloplasty ring further comprises a sliding block for driving the intermediate tube to move, the intermediate tube knob being connected to the first end of the intermediate tube through the sliding block, wherein the intermediate tube is movable within the body of the outer tube through manipulation of the intermediate tube knob to engage the external thread on the intermediate tube with the internal thread of the adjustment member.

16. The delivery system for a prosthetic mitral annuloplasty ring of claim 10, wherein the delivery device for the prosthetic mitral annuloplasty ring further comprises a graduated indicator showing a status of the core knob.

17. The delivery system for a prosthetic mitral annuloplasty ring of claim 10, wherein the adjusting core comprises a first core segment and a second core segment, the first core segment connected to the driving member at one end and coupling with the second core segment at the other end.

18. The delivery system for a prosthetic mitral annuloplasty ring of claim 17, wherein the first core segment is a circular cylinder, and the second core segment has a rectangular, cross-shape or star-shaped cross-section.

19. The delivery system for a prosthetic mitral annuloplasty ring of claim 10, wherein the intermediate tube comprises a first section and a second section coupling with the first section, the first section of the intermediate tube passing through the body of the outer tube along the axial direction of the outer tube, the second section of the intermediate tube projecting out of the body of the outer tube, and wherein the external thread is formed on a wall of the second section of the intermediate tube.

20. The delivery system for a prosthetic mitral annuloplasty ring of claim 10, wherein the adjusting core is fabricated from a nickel titanium alloy, a medical grade stainless steel or a cobalt-based alloy.

* * * * *